(12) United States Patent
Rettedal et al.

(10) Patent No.: US 12,220,261 B2
(45) Date of Patent: Feb. 11, 2025

(54) LIVESTOCK HEART RATE MEASUREMENT WITH BOLUS SENSOR

(71) Applicant: ST Reproductive Technologies, LLC, Navasota, TX (US)

(72) Inventors: Nicholas P. Rettedal, Berthoud, CO (US); Stephen M. Weilnau, Greeley, CO (US); Joseph J. Janus, IV, Windsor, CO (US); Randall Bond, Hilliard, OH (US)

(73) Assignee: ST Reproductive Technologies, LLC, Navasota, TX (US)

( * ) Notice: Subject to any disclaimer, the term of this patent is extended or adjusted under 35 U.S.C. 154(b) by 136 days.

(21) Appl. No.: 17/443,391

(22) Filed: Jul. 26, 2021

(65) Prior Publication Data

US 2023/0027278 A1    Jan. 26, 2023

(51) Int. Cl.
*A61B 5/00* (2006.01)
*A61B 5/024* (2006.01)
(Continued)

(52) U.S. Cl.
CPC .............. *A61B 5/721* (2013.01); *A61B 5/024* (2013.01); *A61B 5/073* (2013.01); *A61B 5/6861* (2013.01);
(Continued)

(58) Field of Classification Search
CPC . A61B 5/024; A61B 5/02444; A61B 5/02455; A61B 5/0255; A61B 5/073; A61B 5/113; A61B 5/6861; A61B 5/721; A61B 5/7225; A61B 5/7246; A61B 5/725; A61B 5/746; A61B 2503/40; A61B 2562/0219;
(Continued)

(56) References Cited

U.S. PATENT DOCUMENTS

| 5,482,008 A | 1/1996 | Stafford et al. |
| 5,532,692 A | 7/1996 | Tatsuya |

(Continued)

FOREIGN PATENT DOCUMENTS

| WO | 2011079338 A2 | 7/2011 |
| WO | 2011130771 A1 | 10/2011 |

(Continued)

OTHER PUBLICATIONS

Boehmer et al. Effects of Temperature of Consumed Water on Rumen Temperature of Beef Cows. Oklahoma Agricultural Experiment Station, 2009, 4 total pages.

(Continued)

*Primary Examiner* — May A Abouelela
*Assistant Examiner* — Anna Roberts
(74) *Attorney, Agent, or Firm* — Ryan Christensen; Hashim Rahman

(57) ABSTRACT

Various examples describe a livestock monitoring system and method. A sensor signal may comprise a rotational component describing a rotation of the sensor within an animal and a linear component describing a linear movement of the sensor within the animal. The rotational component may be used to identify an animal respiration signal. The animal respiration signal and the linear component may be used to generate a respiration-corrected linear component. An animal heart signal may be detected from the respiration-corrected linear component.

20 Claims, 9 Drawing Sheets

(51) Int. Cl.
 *A61B 5/07* (2006.01)
 *G06K 7/10* (2006.01)
 *G06K 19/07* (2006.01)

(52) U.S. Cl.
 CPC ............ *A61B 5/7246* (2013.01); *A61B 5/725* (2013.01); *G06K 7/10366* (2013.01); *G06K 19/0723* (2013.01); *A61B 2503/40* (2013.01); *A61B 2562/0219* (2013.01)

(58) Field of Classification Search
 CPC ........... G06K 7/10366; G06K 19/0717; G06K 19/0723
 See application file for complete search history.

(56) References Cited

U.S. PATENT DOCUMENTS

| | | | |
|---|---|---|---|
| 5,697,384 | A | 12/1997 | Miyawika |
| 5,963,132 | A | 10/1999 | Yoakum |
| 5,984,875 | A | 11/1999 | Brune |
| 6,059,733 | A | 5/2000 | Brune |
| 6,099,482 | A | 8/2000 | Brune |
| 6,371,927 | B1 | 4/2002 | Brune et al. |
| 7,441,515 | B2 | 10/2008 | Renz et al. |
| 7,920,913 | B1 | 5/2011 | Nabutovsky |
| 8,545,436 | B2 | 10/2013 | Robertson et al. |
| 8,588,887 | B2 | 11/2013 | Arneson et al. |
| 8,640,712 | B2 | 2/2014 | Ardrey, Jr. |
| 8,694,091 | B2 | 4/2014 | Birk et al. |
| 8,771,201 | B2 | 7/2014 | Gabriel et al. |
| 9,451,892 | B2 | 9/2016 | Siejko |
| 9,504,231 | B2 | 11/2016 | Rosenkranz et al. |
| 9,619,213 | B2 | 4/2017 | Gupta et al. |
| 10,231,644 | B2 | 3/2019 | Rettedal |
| 10,390,515 | B2 | 8/2019 | Bancroft et al. |
| 10,548,509 | B2 | 2/2020 | Rettedal |
| 2004/0133131 | A1 | 7/2004 | Kuhn et al. |
| 2004/0155782 | A1 | 8/2004 | Letkomiller et al. |
| 2005/0209521 | A1* | 9/2005 | Kettunen ............ A61B 5/7278 600/508 |
| 2006/0185605 | A1 | 8/2006 | Renz et al. |
| 2007/0156016 | A1 | 7/2007 | Betesh et al. |
| 2008/0236500 | A1 | 10/2008 | Hodges et al. |
| 2009/0182207 | A1 | 7/2009 | Riskey et al. |
| 2009/0187392 | A1 | 7/2009 | Riskey et al. |
| 2020/0113481 | A1* | 4/2020 | Rettedal ............. A01K 11/007 |
| 2023/0053966 | A1* | 2/2023 | Pless .................. A61M 31/002 |
| 2023/0119173 | A1* | 4/2023 | Dieken ................ A61B 5/686 607/42 |

FOREIGN PATENT DOCUMENTS

| | | |
|---|---|---|
| WO | 2012173502 A1 | 12/2012 |
| WO | 2017124126 A1 | 7/2017 |
| WO | 2020097655 A1 | 5/2020 |

OTHER PUBLICATIONS

Caja et al. Development of a ceramic bolus for the permanent electronic identification of sheep, goat and cattle. Computers and Electronics in Agriculture (1999), vol. 24, pp.

Carne et al. Modeling the retention of rumen boluses for the electronic identification of goats. J Dairy Sci, Feb. 2011, 94(2), pp. 716-726 (abstract only, 2 pages total).

Cooper-Prado, et al. Relationship of Ruminal Temperature with Parturition and Estrus of Beef Cows. J Anim Sci, Apr. 2011, 89:1020-1027; published ahead of print Dec. 17, 2011.

Hach. Digital Inductive Conductivity Sensor, Convertible Body Style. Website, http:/www.hach.com, product page downloaded Mar. 5, 2014, 2 total pages.

Fallon et al. Electronic Animal Identification. Grange Research Center, Beef Production Series No. 46, pp. 1-54.

Ghirardi et al. Evaluation of the retention of electronic identification boluses in the forestomachs of cattle. Journal of Animal Science (2006), vol. 84, pp. 2260-2268.

Ghirardi et al. Retention of different sizes of electronic identification boluses in the forestomachs of sheep. J Anim Sci, Nov. 2006, 84(10), pp. 2865-2872.

Scanga et al. Development of computational models for the purpose of conducting individual livestock and premises traceback investigations utilizing National Animal System compliant data. Journal of Animal Science, Dec. 2007, vol. 85, Issue 12, pp. 503-511.

Smartstock USA. Website, http://www.smartstock-usa.com, originally downloaded Dec. 30, 2011, 12 total pages.

Lefcourt et al. "A Noninvasive Radiotelemetry System to Monitor Heart Rate for Assessing Stress Responses of Bovines." J Dairy Sci. vol. 82. 1999. pp. 1179-1187.

Wierig et al. "Recording Heart Rate Variability of Dairy Cows to the Cloud—Why Smartphones Provide Smart Solutions." Sensors, 18, 2541, 2018.

International Search Report and Written Opinion issued on Oct. 26, 2022 in related PCT Appl. No. PCT/US22/37808.

Lefcourt, Alan M., et al., "A Noninvasive Radiotelemetry System to Monitor Heart Rate for Assessing Stress Responses of Bovines", J Dairy Sci 82, (1999), 1179-1187.

* cited by examiner

LIVESTOCK HEART RATE MEASUREMENT WITH BOLUS SENSOR

BACKGROUND

It may be desirable to know the heart rate of livestock to monitor the health of the livestock. Measuring the heart rate of livestock however, especially the heat rate of large animals, can be challenging. Manually measuring the heart rate of a cow, for example, can include sequestering the animal from other members of its herd and then restraining the animal to allow a veterinarian or other technician to place a stethoscope. The technician keeps the stethoscope in place for a predetermined period of time and counts the animal's heartbeats to determine the heart rate, for example, in beats per minute. Even with these steps, the result is a measurement reflecting the animal's heart rate, but just at the time that the measurement was taken. Also, the process of sequestering the animal and taking the measurement can induce stress, which can affect the animal's heart rate and thereby affect the accuracy of the measurement.

BRIEF DESCRIPTION OF DRAWINGS

The present disclosure is illustrated by way of example and not limitation in the following figures.

DETAILED DESCRIPTION

Figure 1:
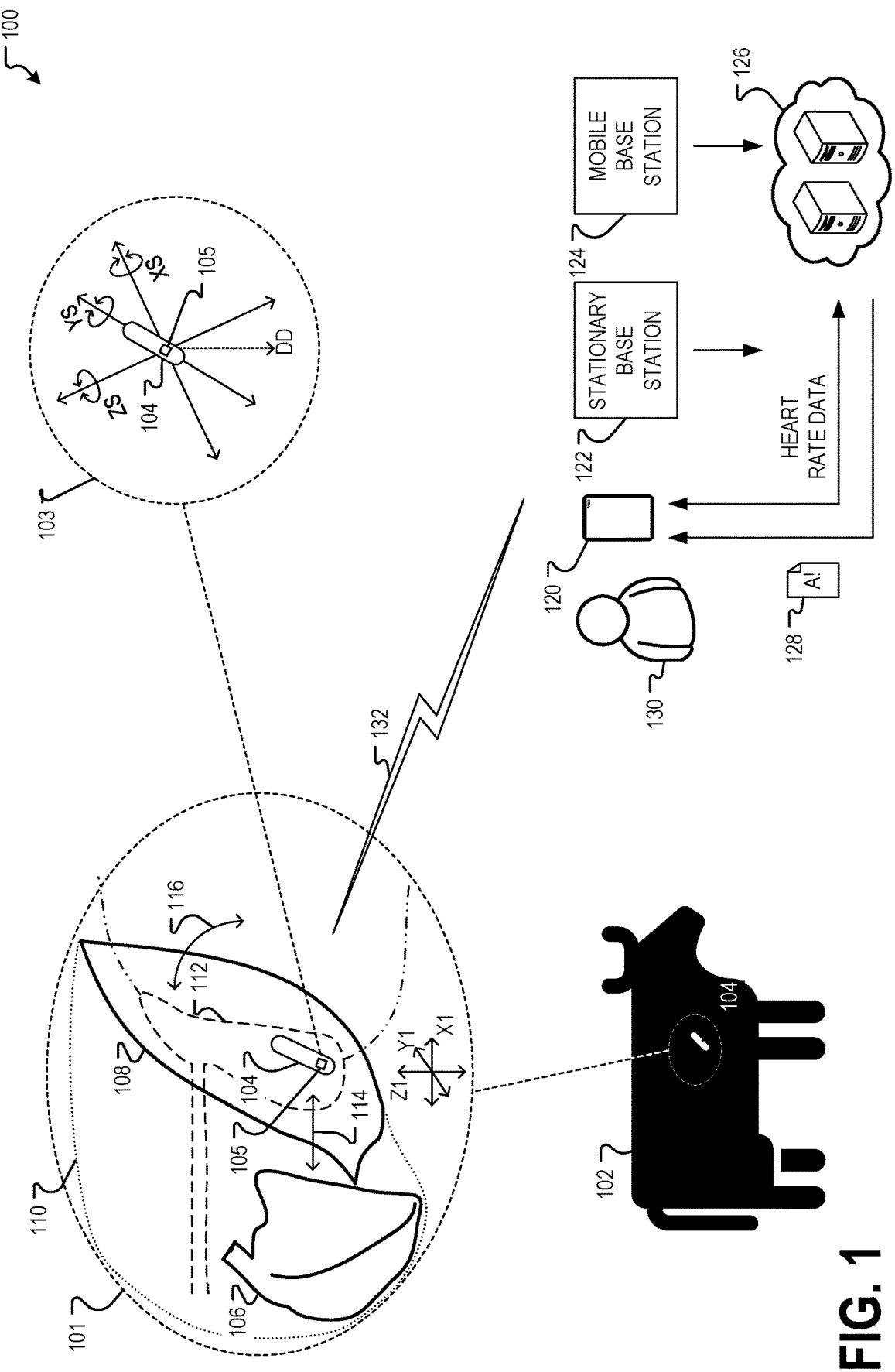
FIG. 1 is a diagram showing one example of an environment for measuring the heart rate of an animal using a bolus.

Various sensors and techniques are described herein for measuring, and in some examples, continuously monitoring the heart rate of an animal in a manner that is suitable for consistent and accurate measurement.

One example solution to the difficulties of manual heart rate measurement in livestock is to use a sensor to detect animal heart rates. Common heart rate sensors used for humans, however, exhibit new problems when applied to animals.

For example, some sensors detect heartbeats by detecting electrical activity on the skin. A sensor comprising one or more electrodes is positioned in direct contact with the skin. While direct skin contact can be achieved for human use, it is often more difficult with animals. For example, it may be necessary to shave a spot on the animal in order to maintain suitable electrical contact between the skin and the electrodes. Also, the electrodes may irritate the animal, causing the animal to rub or scrape the device, breaking the electrical connection to the skin.

Other example sensors detect heartbeats using an optical device that measures differences in color under the skin due to blood flow. The heartbeat and heart rate information can be extrapolated from the timing of the color changes. When applied to livestock, optical-based sensors suffer from disadvantages similar to those of electrode-based sensors. For example, optical sensor performance may be best when the sensors have good skin contact in a consistent location where there are veins, arteries, or capillaries under the skin. Keeping a sensor consistently placed in such an area on an animal's skin can be challenging.

In various examples, these and other challenges can be addressed by using a bolus to measure an animal's heart rate. A bolus is a device that can be ingested by an animal and remains in the animal's digestive tract for a period of time. Some boluses are designed for use with ruminants such as cattle, sheep, and the like and can remain in the animal's reticulum or other pre-stomach organ. The bolus can include one or more sensors for measuring conditions of the animal's digestive tract including, for example, pH data describing the pH of the animal's digestive tract, partial pressure data indicating the partial pressure of dissolved gasses in the animal, motion data indicating a motion of the sensor, temperature data indicating the temperature at the animal's digestive tract, and so forth.

In various examples, an accelerometer or other motion sensor present at a bolus is used to measure the heart rate of an animal. For example, the motion of the animal's heart beats may be transmitted through the animal's tissue to the reticulum or other digestive tract location of the bolus and detected by the bolus motion detector. Heartbeats, however, are not the only motion transmitted to the bolus. When the animal breathes, its diaphragm muscle contracts and releases to alternately fill and empty the animal's lungs. The motion of the animal's diaphragm and lungs can also be transmitted to the bolus. Also, the animal's digestive tract itself contracts and releases to move food and other digestive materials. Other motion due to the animal walking, running, or otherwise moving can also be transmitted to the digestive tract and captured by a bolus sensor.

A further challenge with using a bolus sensor to detect an animal's heartbeat is that the bolus itself can assume different orientations in an animal's digestive tract depending on the dimensions and shape of the bolus, the dimensions and shape of the animal's digestive tract, and even the stage of the animal's digestive process. Accordingly, the reference frame for the motion sensor does not necessarily match the reference frame of the animal. Accordingly, even if directional information about the animal's heartbeat, breathing, and/or digestive motions are known in the animal's reference frame, determining how these motions relate to the bolus reference frame is often nontrivial.

FIG. 1 is a diagram showing one example of an environment 100 for measuring the heart rate of an animal 102 using a bolus 104. The bolus 104 may include various sensors including, for example, a motion sensor 105. The motion sensor 105 may be or include an accelerometer. The motion sensor 105 generates a sensor signal reflecting the acceleration of the motion sensor 105. The sensor signal includes a rotational component and a linear component. The linear component of the sensor signal describes an acceleration of the motion sensor 105 in three-dimensional (3D) space. The rotational component describes an acceleration of the motion sensor 105 about the three dimensions.

FIG. 1 also shows a breakout window 101 illustrating various organs of the animal 102 including, for example, a heart 106, a diaphragm 108, lung 110, and reticulum 112. In this example, the bolus 104 is positioned in the reticulum 112. When the heart 106 beats, it causes linear motion in the direction indicated by arrow 114. The linear motion of the heart 106 is transmitted by the tissue of the animal 102 to the digestive tract where it causes the bolus 104 and motion sensor 105 to accelerate linearly. Accordingly, linear motion from the heart 106 may be reflected in the linear component of the sensor signal.

When the animal 102 breathes, the diaphragm 108 causes the lungs 110 to expand and contract to take-in and expel air for respiration. The expansion and contraction of the diaphragm 108 occurs as motion indicated by the arrow 116. This motion is also transmitted by the animal's tissue to the digestive tract of the animal 102. Because of the animal's respiration and the relative position of the animal's organs, the motion of respiration (e.g., indicated by arrow 116) causes the bolus 104 and motion sensor 105 to accelerate linearly and rotationally. Accordingly, motion from respiration may reflected in both the linear component and in the rotational component of the sensor signal.

The sensor signal is provided from the bolus 104 to a receiving component. For example, a wireless connection 132 may be established between the bolus 104 and the receiving component. The sensor signal (and/or various pre-processed derivatives of the sensor signal) may be transmitted via the wireless connection 132. Any suitable wireless connection 132 may be used including, for example, an active RFID connection, a passive RFID connection, a Near Field Communication (NFC) connection, a Bluetooth® connection, a Bluetooth LE® connection, and/or the like.

Various different types of receiving components can be used including, for example, a user computing device 120, a stationary base station 122, and/or a mobile base station 124. A stationary base station 122 may be or include a computing device as well as a receiver or transceiver for establishing the wireless connection 132 to the bolus 104. The stationary base station 122 may also include hardware for making another wired and/or wireless connection to a livestock measurement server 126, for example, via a wide area network (WAN).

A stationary base station 122 may be positioned at a stationary location, for example, where the animal 102 is expected to be present on a regular basis. For example, a stationary base station 122 may be positioned at a feeding location, in a milking parlor, or another location where the animal 102 is expected to be regularly. When the animal 102 comes within a threshold distance of a stationary base station 122, the stationary base station 122 may establish a wireless connection 132 with the bolus 104 to receive the sensor data.

In some examples, a mobile base station 124 can be used as a receiving component. A mobile base station 124 may be or include a computing device as well as a receiver or transceiver for establishing the wireless connection 132 to the bolus 104. The mobile base station 124 may also include hardware for making a wired and/or wireless connection to the livestock management server 126. The mobile base station 124 may be positioned, for example, on a tractor, truck, or other vehicle that moves in areas frequented by the animal 102. For example, an agriculture technician may move a mobile base station 124 though a herd including the animal 102 to collect sensor signals from the animal 102 and/or from other animals in the herd.

In some examples, a user computing device 120 can be used as a receiving component. The user computing device 120 may comprise a receiver and/or transceiver for establishing the wireless connection 132 to the bolus 104. The user computing device may also include hardware for making a wired or wireless connection to the livestock management server 126. In some examples, the user computing device is or includes any suitable computing device or devices such as, for example, a smart phone, a tablet computer, a laptop computer, a smart watch, and so forth.

The user computing device 120 may also comprise input/output (I/O) devices for providing a graphical user interface (GUI) the user 130. For example, the user computing device 120 may comprise a display for providing the GUI to the user 130. In some examples, the user computing device 120 is or comprises a display that is configured to be worn on the user's head, such as a heads-up display, smart glasses display, or similar display.

The user 130 may bring the user computing device 120 into the proximity of the animal 102 to allow the wireless connection 132 between the user computing device 120 and the bolus 104. A sensor signal from the motion sensor 105 may be provided to the user computing device via the wireless connection 132, as described herein.

The user computing device 120, stationary base station 122, and/or mobile base station 124 may be in communication with the livestock management server 126 to provide sensor signal data and/or heart rate data to the livestock management server 126. The livestock management server 126 may store sensor signal data and/or heart rate data for the animal 102. In some examples, the livestock management server 126 is configured to provide heart rate data to the user computing device 120. The livestock management server 126, in this example, provides the heart rate data for the animal 102 to the user computing device 120 that may also serve as a receiving component and/or to a different user computing device.

A user 130 of the user computing device 120 may view the heart rate data to monitor the health of the animal 102. For example, the user 130 may be a veterinarian or other veterinary technician who is treating the animal 102. The heart rate data may be used, for example, to diagnose and/or treat a health condition of the animal 102.

In some examples, the livestock management server 126 is also configured to provide an alert 128 to the user computing device 120. For example, if the heart rate of the animal 102 is outside of a desirable range and/or outside of the desirable range for more than a threshold period of time, the livestock management server 126 may send the alert 128 to the user computing device 120. This may prompt the user 130 to examine the animal 102, for example, to diagnose an animal health condition causing the animal heart rate to be outside of the desired range.

In various examples, one or more components of the environment 100 are programmed to detect the animal's heartbeat from the sensor signal. The animal's heart rate can then be measured, for example, by counting heartbeats over a given time period. Generating the animal heart signal can include correcting the sensor signal to remove motion components due to respiration. Recall that the respiration of the animal 102 results in a motion affecting the linear component and the rotational component of the sensor signal. In various examples, the rotational component of the sensor signal is used to identify a respiration signal indicating the animal's respiration. The respiration signal can identify the timing (e.g., frequency and offset) of respiration artifacts in the linear component of the sensor signal. The respiration artifacts can be removed from the linear component to generate a respiration-corrected linear component. The respiration-corrected linear component may reflect the heart beats of the animal 102. For example, artifacts remaining in the respiration-corrected linear component may be the result of animal 102 heartbeats.

In various examples, determining the animal's heartbeat includes correcting for differences between a sensor frame and the base frame of the animal 102. For example, the sensor signal, including the linear component and the rotational component, is referenced to a sensor frame. The sensor frame is shown in breakout window 103 and includes axes XS, YS, and ZS. For example, the linear component of the sensor signal indicates acceleration of the motion sensor 105 along the XS axis, along the YS axis, and along the ZS axis. The rotational component of the sensor signal indicates rotational acceleration of the motion sensor 105 about the XS axis, rotational acceleration of the motion sensor 105 about the YS axis, and rotational acceleration of the motion sensor 105 about the ZS axis. The direction of the sensor frame axes XS, YS, ZS depends on the orientation of the bolus 104 and sensor 105 in the digestive tract of the animal 102.

The motion generated by the functions of the animal 102 is referenced to a base frame indicated by axes X1, Y1, and Z1. For example, one might know the general direction of the rotational and linear acceleration caused by respiration (e.g., arrow 116), but those directions may be known relative to the base frame axes X1, Y1, Z1. Because the orientation of the bolus 104 and sensor 105 is not known, directions known in the base frame may not be known or easily detectible in the sensor frame.

In various examples, this challenge is addressed by considering the magnitude of the sensor signal. For example, a magnitude component may be determined for both the linear component and the rotational component of the sensor signal, resulting in a rotational magnitude and a linear magnitude. Magnitude signals may indicate the magnitude of sensor acceleration independent of direction. Magnitude signals can be derived in any suitable manner. For example, a linear magnitude component can be or be based on the magnitude of the vector indicating the linear acceleration of the sensor 105 in the sensor space. A rotational magnitude component can be or be based on the magnitude of the vector indicating the rotational acceleration of the sensor 105 in the sensor space. Accordingly, the linear magnitude component and rotational magnitude component may be independent of direction.

Using magnitude components, such as the linear and/or rotational magnitude components described herein, may allow the heartbeat of the animal 102 to be detected without regard to the orientation of the bolus 104 and sensor 105 in the digestive tract of the animal 102. For example, peaks of the linear magnitude component may reflect the respiration events of the animal 102. The timing of the respiration events indicated by peaks in the rotational magnitude component can be correlated to corresponding peaks in the linear magnitude components. The corresponding peaks in the linear magnitude components can be filtered or otherwise removed to generate the respiration-corrected linear component.

In other examples, the sensor data is used to detect a down direction in the sensor frame, indicated in FIG. 1 by the line DD. The down direction is the direction of gravitational acceleration and may be parallel to the Z1 axis in the base frame. For example, the line DD may be parallel to the Z1 axis of the base frame. Knowing the down direction in the sensor frame may allow some or all of the sensor signal to be translated from the sensor frame to the base frame and/or allow the expected rotational direction of the animal respiration events to be translated from the base frame to the sensor frame.

The translation from the sensor frame to the base frame may be used to identify peaks in the rotational component due to the animal's respiration. This may provide the timing of respiration events. The timing can be used to identify peaks in the linear component that are caused by the respiration event (e.g., in the raw linear component and/or a linear magnitude component). The corresponding peaks may be removed from the linear component to generate heartbeat data showing the animal 102 heartbeat.

Depending on the implementation, the heartbeats and/or heart rate of the animal 102 can be determined as described herein by various different components of the environment 100. For example, the motion sensor 105 and/or bolus 104 may provide a raw sensor signal including the linear and rotational component and/or may comprise processing hardware for generating heart rate data for the animal 102 and/or performing some of the actions described herein for generating animal heart rate data. For example, the motion sensor 105 and/or bolus 104 may comprise hardware for implementing one or more state machines. In some examples, the motion sensor 105 and/or bolus 104 generates rotational and linear components and provides the rotational and linear components to the receiving component. In some examples, the motion sensor 105 and/or bolus 104 generates linear and/or rotational magnitude components and provides the linear and/or rotational magnitude components to the receiving component. In some examples, the motion sensor 105 and/or bolus 104 derives the down direction and provides an indication of the down direction to the receiving component. In some examples, the motion sensor 105 and/or bolus 104 detects heartbeats and/or heart rate, as described herein, and provides the heartbeats and/or heart rate to the receiving component.

Also, in some examples, the receiving component (e.g., user computing device 120, stationary base station 122, and/or mobile base station 124) may be programmed to perform some or all of the processing for generating heart rate data. For example, the receiving component may generate linear and/or rotational magnitude components and provide the linear and/or rotational magnitude components to the livestock management server 126. In some examples, the receiving component derives the down direction and provides an indication of the down direction to the livestock management server 126. In some examples, the receiving component detects heartbeats and/or heart rate, as described herein, and provides the heartbeats and/or heart rate to the livestock management server 126.

In some examples, the livestock management server 126 performs some or all of the processing for generating heart rate data. For example, the livestock management server 126 may receive a sensor signal with linear and rotational components and generate linear and/or rotational magnitude components. In some examples, the livestock management server 126 derives the down direction. In some examples, the livestock management server 126 detects heartbeats and/or heart rate, as described herein.

Figure 2:
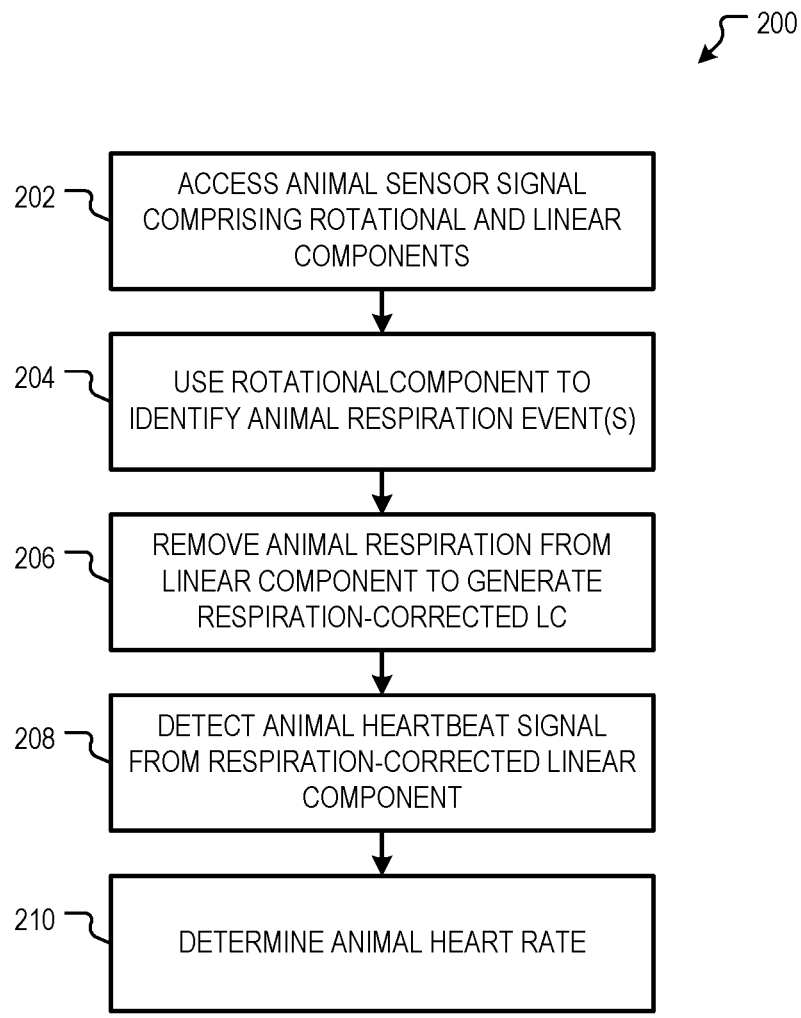
FIG. 2 is a flowchart showing one example of a process flow that may be executed to determine heart rate data for the animal using a bolus.

FIG. 2 is a flowchart showing one example of a process flow 200 that may be executed to determine heart rate data for the animal 102 using a bolus. The operations of the process flow 200 may be performed by various components of the environment 100 of FIG. 1 such as, for example, by the motion sensor 105, by the bolus 104, by the receiving component, and/or by the livestock management server 126.

At operation 202, animal sensor signal data is accessed. The animal sensor signal data may be or include a sensor signal generated by the motion sensor 105. As described herein, the motion sensor 105 may be positioned on, in, or otherwise associated with the bolus 104. The sensor signal data may comprise a linear component indicating the linear acceleration of the motion sensor and a rotational component indicating rotational acceleration of the motion sensor 105.

At operation 204, the rotational component is used to identify an animal respiration signal. The animal respiration signal indicates the timing of animal respiration events. The animal respiration signal can be determined in various ways. In some examples, a rotational magnitude component is used to generate the animal respiration signal, for example, as described in more detail with respect to the process flow 300. In other examples, a down direction is derived in the sensor frame and used to identify animal respiration events, as described in more detail with respect to the process flow 400.

At operation 206, the animal respiration signal is used to remove peaks corresponding to the animal respiration events from the linear component of the sensor signal. For example, respiration events determined at operation 204 can be correlated to corresponding peaks in the linear component that occur at the same time. These peaks may be removed from the linear component, resulting in a respiration-corrected linear component.

At operation 208, an animal heartbeat signal is generated using the respiration-corrected linear component. For example, various additional filtering may be performed to remove additional artifacts from the respiration-corrected linear component such as, for example, motion artifacts due to digestion or other biological processes, motion artifacts do to the animal moving, and the like. In some examples, some or all of the additional filtering is performed on the linear component before the respiration-corrected linear component is generated. At operation 210, an animal heart rate is determined. The animal heart rate can be determined, for example, by counting peaks in the respiration-corrected linear component.

Figure 3:
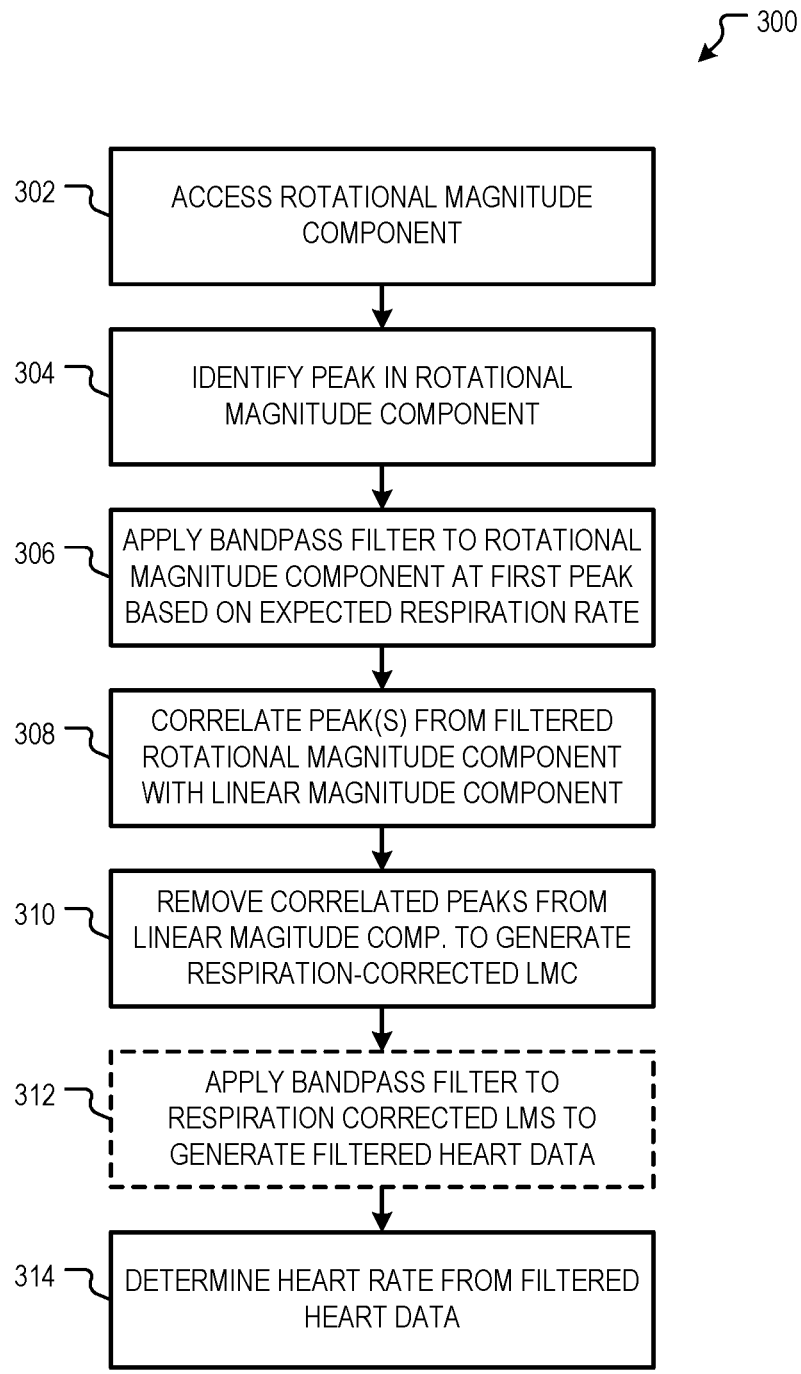
FIG. 3 is a flowchart showing one example of a process flow that may be executed to determine heart rate data for the animal using a bolus and sensor magnitude data.

FIG. 3 is a flowchart showing one example of a process flow 300 that may be executed to determine heart rate data for the animal 102 using a bolus and sensor magnitude data. The operations of the process flow 200 may be performed by various components of the environment 100 of FIG. 1 such as, for example, by the motion sensor 105, by the bolus 104, by the receiving component, and/or by the livestock management server 126.

At operation 302, a rotational magnitude signal is accessed. The rotational magnitude signal indicates the magnitude of rotation of the motion sensor 105, for example, independent of direction. In some examples, the rotational magnitude signal is generated from a rotational component of a raw sensor signal including rotation components about X, Y, and Z axes where the X, Y, and Z axes are according to the position of the bolus 104 within the animal 102.

At operation 304, a peak in the rotational magnitude component is identified. The peak can be detected in any suitable manner. In some examples, the peak is determined by examining a first derivative of the rotational magnitude component. For example, a peak may be detected at a point in the rotational magnitude component where the first derivative transitions from positive to negative. In some examples, the identified peak is the first high-quality (High-Q) peak identified in the rotational magnitude component. A High-Q peak may be a peak with greater than a threshold percent change of being above the noise floor.

Other peak detection techniques may be used in addition to or instead of the High-Q technique. For example, an expected mean value may be found along with a delta threshold indicating an expected high level of the rotational magnitude component. Peaks may be detected at portions of the rotational magnitude component having greater than the expected mean value by more than the delta threshold. In another example, the mean value of the rotational magnitude component may be found. Portions of the rotational magnitude component that are greater than two standard deviations higher than the mean may be detected as peaks.

At operation 306, a bandpass filter is applied to the rotational magnitude component. The passband of the bandpass filter may be selected based on an expected respiration rate of the animal 102. For example, a cow may be expected to breathe between ten and thirty times per minute. Accordingly, when the animal 102 is a cow, the bandpass filter applied to the rotational magnitude component may have a passband of between about 10 Hz and about 30 Hz. The bandpass filtering at operation 306 may tend to remove from the rotational magnitude component any events that are not caused by respiration. In some examples, the bandpass filter is applied beginning at the peak identified at operation 304.

At operation 308, peaks from the filtered rotational component are identified and correlated with corresponding peaks in a linear magnitude component. Correlated peaks may be peaks that occur at or near the same time. Consider an example in which an identified peak in the filtered rotational magnitude component occurs at a time t in the filtered rotational magnitude component. Correlating the example peak to a corresponding peak in the linear magnitude component may include identifying a peak in the linear magnitude component that occurs at or near the time t, for example, within t±i, where i is a threshold time.

Like the rotational magnitude component, the linear magnitude component may be calculated from a raw linear component of the sensor signal indicating linear acceleration in three dimensions. The linear magnitude component, in some examples, is generated directly by the motion sensor 105. The peaks from the linear magnitude component and the correlated peaks in the filtered rotational magnitude component may be caused by the same respiration events.

At operation 310, the peaks of the linear magnitude component that correlate to corresponding peaks in the filtered rotational component are filtered or otherwise removed from the linear magnitude component to generate a respiration-corrected linear magnitude component. At optional operation 312, a bandpass filter is applied to the respiration-corrected linear magnitude component. The passband of the bandpass filter applied at operation 312 may be based on an expected heart rate range for the animal 102. The bandpass filter applied at optional operation 312 may remove non-respiration and non-heartbeat artifacts from the respiration-corrected linear magnitude component. It will also be appreciated that the bandpass filter at operation 312 may, in some examples, be applied before respiration correction is performed at operations 308 and 310. At operation 314, an animal heart rate is determined. The animal heart rate can be determined, for example, by counting peaks in the respiration-corrected linear component over a constant period of time.

Figure 4:
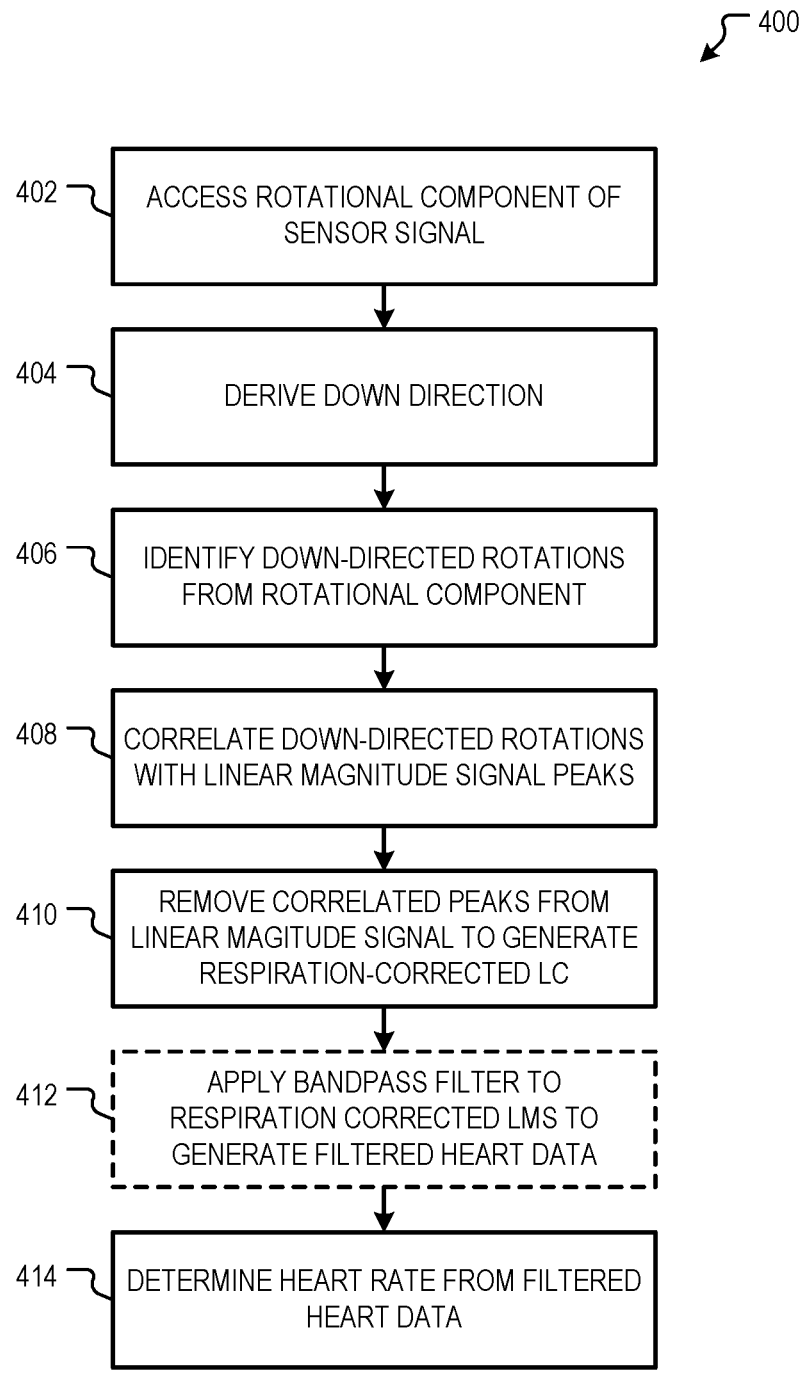
FIG. 4 is a flowchart showing one example of a process flow that may be executed to determine heart rate data for the animal using a bolus by determining a down direction.

FIG. 4 is a flowchart showing one example of a process flow 400 that may be executed to determine heart rate data for the animal 102 using a bolus by determining a down direction. The operations of the process flow 200 may be performed by various components of the environment 100 of FIG. 1 such as, for example, by the motion sensor 105, by the bolus 104, by the receiving component, and/or by the livestock management server 126. At operation 402, the rotational component of the sensor signal is accessed. The rotational component may include an indication of rotation referenced to the sensor frame axes XS, YS, ZS. For example, the rotational component may indicate an acceleration about the XS axis, an acceleration about the YS axis, and an acceleration about the ZS axis.

At operation 404, the down direction (DD) is derived based on the rotational component. For example, gravity makes a contribution to the acceleration of the sensor 105 by pulling the sensor down. The contribution of gravity to the acceleration may be constant over time as gravity is constant. Accordingly, determining the down direction may include low-pass filtering of the rotational component. The remaining rotational acceleration indicates a constant portion of the total rotational component and may represent the acceleration due to gravity. The direction of the remaining rotational acceleration may be the down direction.

At operation 406, down-directed peaks in the rotational component are identified. Referring back to FIG. 1 and the break-out window 101, it can be seen that the expansion and contraction of the diaphragm 108 tends to cause down-directed rotation on the digestive tract. Accordingly, down-directed peaks in the rotational component of the sensor signal may correspond to respiration events.

At operation 408, the down-directed peaks in the rotational component are correlated to corresponding peaks in the linear component (e.g., the raw linear component and/or a linear magnitude component). Correlating down-directed peaks to corresponding peaks in the linear component can include identifying peaks in the linear component that occur at or about at the same time as the identified down-directed peaks in the rotational component. At operation 410, the correlated peaks identified at operation 408 are removed from the linear component to generate a respiration-corrected linear component.

At optional operation 412, a bandpass filter is applied to the respiration-corrected linear magnitude component. The passband of the bandpass filter applied at operation 412 may be based on an expected heart rate range for the animal 102. The bandpass filter applied at optional operation 412 may remove non-respiration and non-heartbeat artifacts from the respiration-corrected linear magnitude component. It will also be appreciated that the bandpass filter at operation 412 may, in some examples, be applied before respiration correction is performed at operations 406, 408 and 410. At operation 414, an animal heart rate is determined. The animal heart rate can be determined, for example, by counting peaks in the respiration-corrected linear component over a constant period of time.

Figure 5:
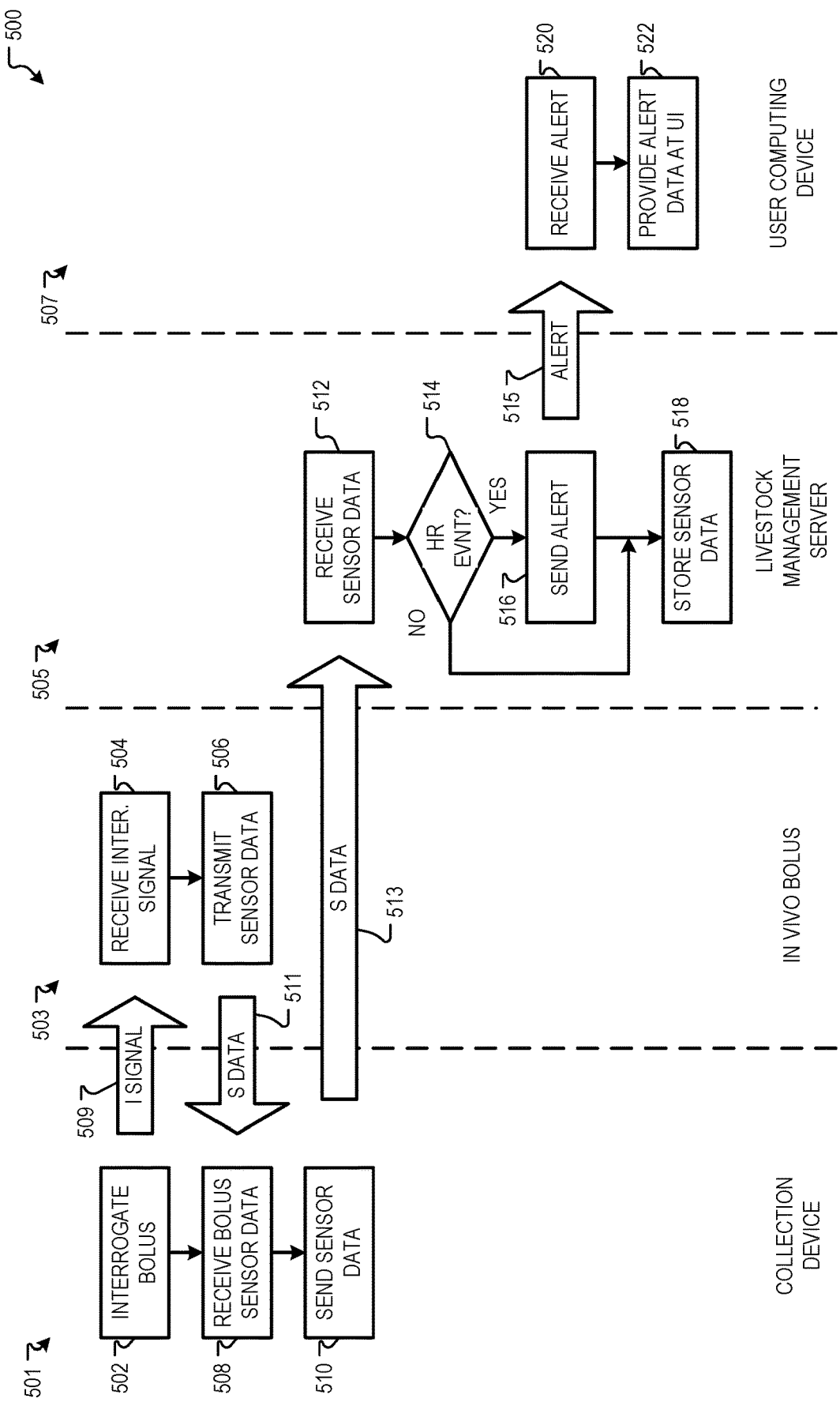
FIG. 5 is a flowchart showing one example of a process flow that may be executed in an environment such as the environment of FIG. 1 to detect animal health events using heartrate data.

FIG. 5 is a flowchart showing one example of a process flow 500 that may be executed in an environment such as the environment 100 of FIG. 1 to detect animal health events using heart rate data. The process flow 500 includes four columns 501, 503, 505, 507 including actions performed by four components. The column 501 includes actions that may be performed by a collection device, such as the user computing device 120, the stationary base station 122, and/or the mobile base station 124. The column 503 includes actions that may be performed by the in vivo bolus 104, which is present within the animal 102. The column 505 includes actions that may be performed by the livestock management server 126. The column 507 includes actions that may be performed by a user computing device, such as the user computing device 120 of the administrative user 130 of FIG. 1.

At operation 502, the collection device interrogates the bolus 104 that is within the animal 102. In this example, the bolus 104 may comprise an RFID circuit, although other types of wireless communication circuits may also be used. Accordingly, the wireless connection 132 between the bolus 104 and the collection device may be or comprise the RFID connection or another suitable wireless connection. Interrogating the bolus 104 may include sending an interrogation signal 509 to the bolus 104. The bolus 104 receives the interrogation signal 509 at operation 504. At operation 506, the bolus 104 replies by sending sensor data 511 to the collection device. The sensor data 511 includes and/or is based on a sensor signal captured by the motion sensor 105 of the bolus 104.

In some examples, the sensor 105 and/or other hardware on the bolus may perform preprocessing of the sensor signal. For example, the sensor data 511 may include the raw sensor signal, a linear component, a rotational component, a linear magnitude component, a rotational magnitude component, a respiration-corrected magnitude component, and so forth. In some examples, the sensor data 511 also includes data captured by other sensors on the bolus 104, such as, for example a temperature sensor, a pH sensor, a heart rate sensor, a partial pressure sensor, and the like. The collection device receives the sensor data at operation 508 and, at operation 510, sends the sensor data 513 to the livestock management server 126. In some examples, the collection device performs some or all of the process described herein with respect to FIGS. 1-4 to derive a heartbeat signal and/or heart rate from the sensor data 511. Accordingly, the sensor data 513 sent to the livestock management server 126 may be the same sensor data 511 received from the bolus 104 and/or may include processed data.

The livestock management server 126 receives the sensor data at operation 512. If the sensor data 513 has not yet been used to derive an animal heartbeat signal or heart rate, the livestock management server 126 may detect the animal's heartbeats and/or the animal's heart rate.

At operation 514, the livestock management server 126 determines if the sensor data indicates a health event. A health event may be detected, for example, if the sensor data is outside of one or more health event ranges. For example, a health event may be detected if the animal's heart rate is outside of an animal heart rate range. Other sensor data from other sensors on the bolus 104 may also be used to detect a health event, e.g., in conjunction with and/or independent of heart rate.

If no health event is detected, the livestock management server 126 stores the receives sensor data at operation 518. If a health event is detected at operation 514, the livestock management server 126, at operation 516, sends an alert message 515 to the user computing device 120. The alert message 515 may be all or part of the alert 128 of FIG. 1. The livestock management server 126 may also store the sensor data at operation 518. In examples where the collection device is a user computing device, such as the user computing device 120, the alert may be sent to the same user computing device that initially received the sensor data 511 from the bolus 104 or to a different user computing device. For example, the alert message 515 may be sent to a user computing device associated with a veterinarian or veterinary technician who is prompted to examine and potentially treat the animal.

The user computing device 120 receives the alert message 515 at operation 520. The alert message 515 may include, for example, an animal identifier of the relevant animal as well as heart rate, temperature, or other raw or derived sensor data received from the bolus 104. The user computing device 120 provides the alert message to the user 130 at operation 522, for example, by displaying some or all of the data from the alert message at a user interface at the user computing device 120. The user 130 may utilize the alert message 515 as a prompt to examine and potentially treat the animal.

Figure 6:
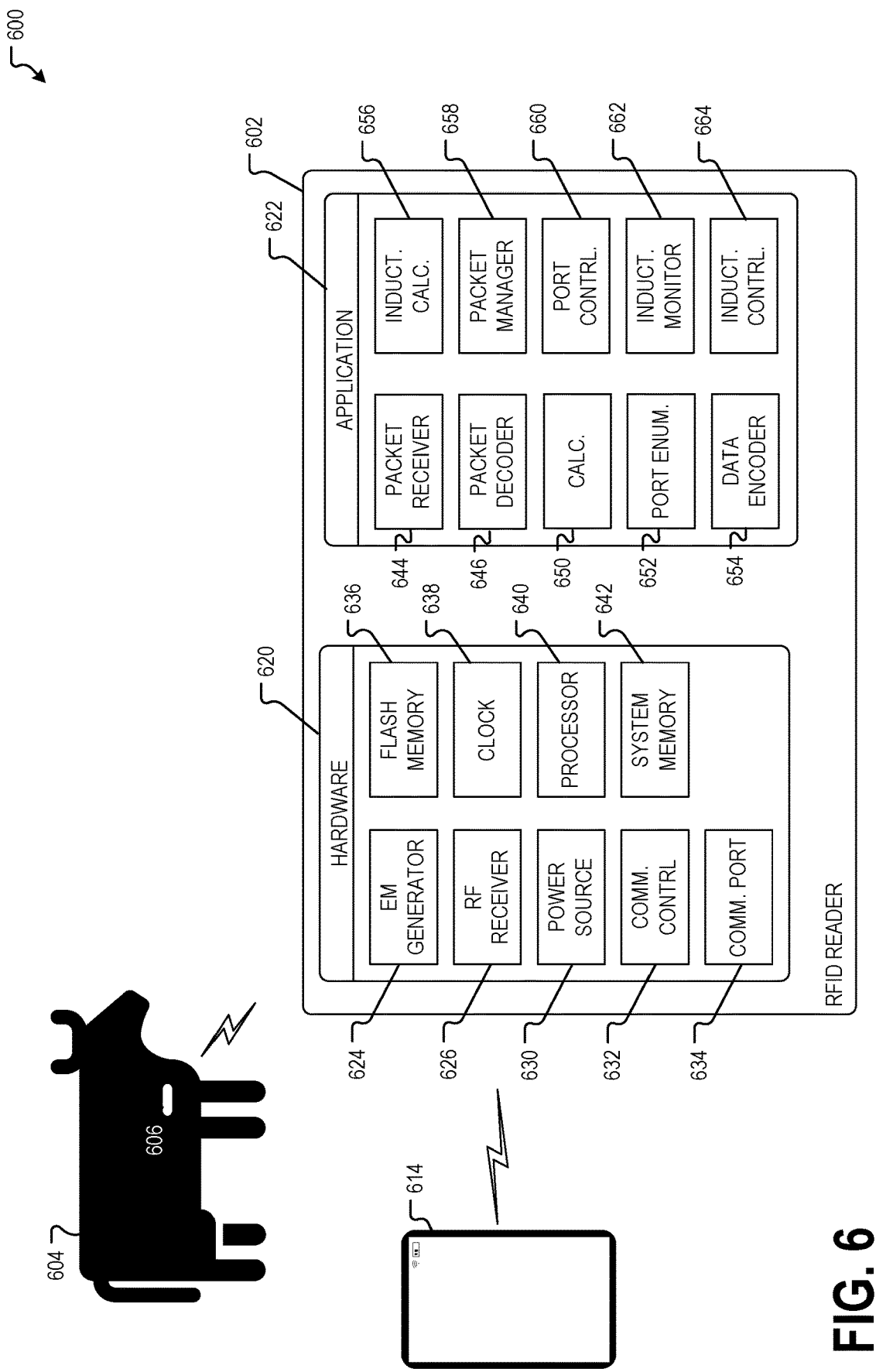
FIG. 6 is a diagram of an environment including a radio frequency identifier (RFID) reader in communication with various RFID devices.
Figure 7:
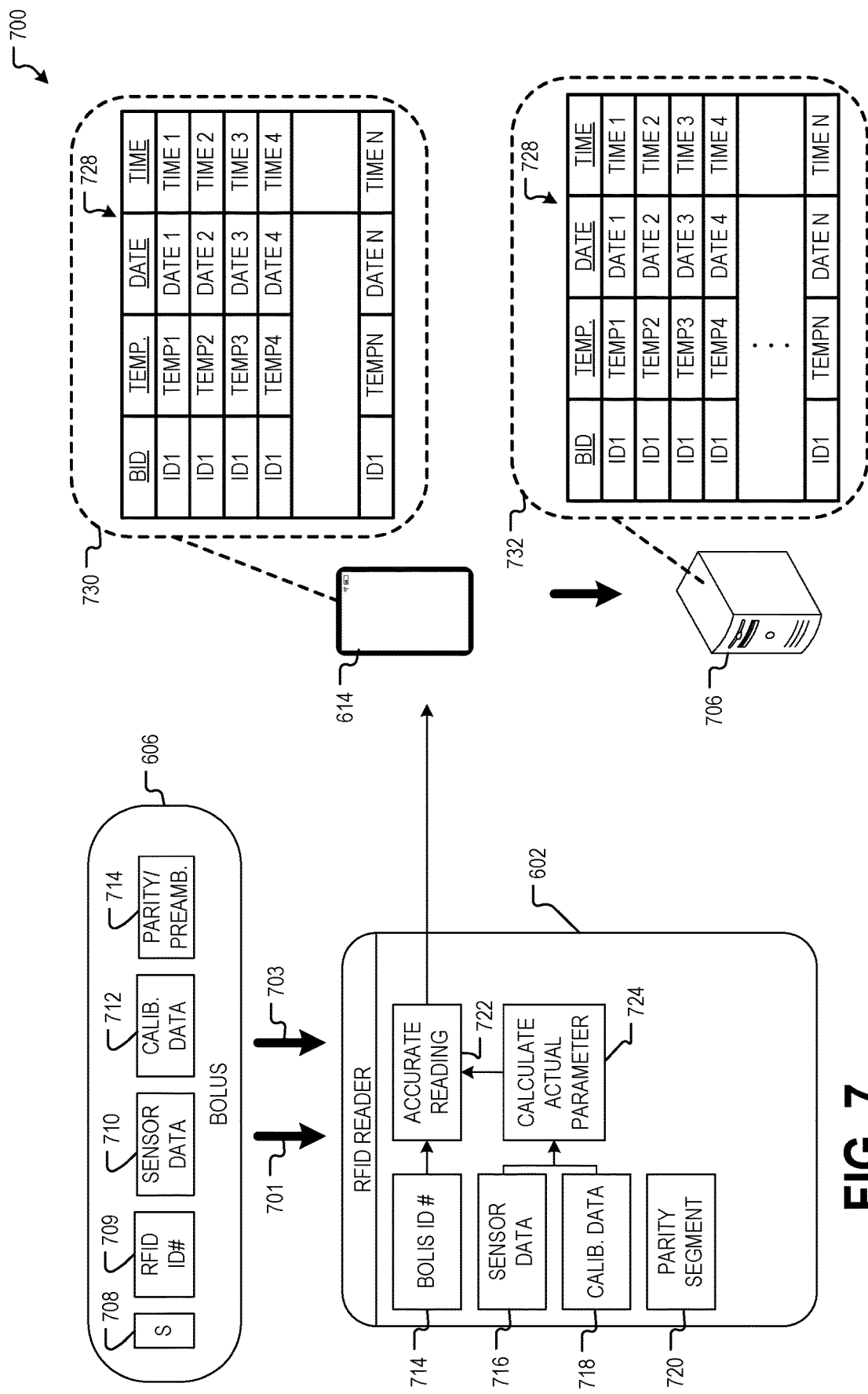
FIG. 7 is a workflow diagram showing one example of RFID data being transferred from an RFID device to a livestock management server via a user computing device.

FIG. 6 is a diagram of an environment 600 including an RFID reader 602 in communication with various RFID devices. In some examples, the RFID reader 602 is a component of a collection device 120, 122, 124. In the example of FIGS. 6 and 7, RFID reader 602 is shown as part of a user computing device 614, which may be similar to the user computing device 120. In other examples, the RFID reader 602 is in communication with a user computing device 614 via a wired or wireless connection. The RFID reader 602 may be configured to wirelessly communicate with various RFID devices. For example, a bolus 606 ingested by an animal 604 may provide sensor data to the RFID reader 602, including sensor data from a motion sensor, such as the motion sensor 105 described herein.

Referring now to FIG. 6, the RFID reader 602 may transmit a radio-frequency carrier signal to the bolus 606 (or another RFID device). The RFID may respond to the radio-frequency carrier signal with a RFID data signal to send and receive an amount of RFID information from the RFID device.

The RFID reader 602 may include hardware 620 and an RFID reader application 622, which may be stored in a memory of the RFID reader 602 as firmware. The hardware 620 may include a processor 640 and system memory 642. The hardware 620 may also include an electromagnetic field generator 624, which comprises an electromagnetic drive antenna for transmitting radio frequency signals. The electromagnetic field generator 624 manages the power level and induction of the electromagnetic drive antenna. In various examples, the electromagnetic drive antenna has an inductance between about 3.5 H and about 4.5 H with a 1-to-4 twist. The hardware 620 may also include a radio frequency signal receiver 626 including a receiving antenna. The radio frequency signal receiver manages the receiving antenna, which collects the RFID information sent by the various RFID devices 606. In another example, the EM generator 624 and radio frequency receiver are consolidated into a single component using a common antenna.

The RFID reader hardware 620 can further include a RFID reader processor 640 which can perform computations based on information 701 and calibration data 703 received from the various RFID devices 606. (See FIG. 7.) A first RFID reader memory 636 can store the amount of RFID information 701 transmitted from the RFID devices 606. In an alternative, the RFID reader processor 640 can integrally include the first RFID reader memory 636. A second RFID reader memory 642 used by the RFID reader processor 640 can perform read-write functions.

The hardware 620 can further include a communication controller 632, which provides communication with a livestock management server 706 (FIG. 7) and/or user computing device 614 via a local area network (LAN) or WAN; and a LAN port or a WAN port 634 for wired or wireless connection to the livestock management server 706 and/or user computing device 614. In alternate embodiments, the RFID reader processor 640 can be programmed to further provide the functionalities of the communication controller 632. The livestock management sever 706 (FIG. 7) may operate in a manner similar to the livestock management server 126.

A clock 638 can function to govern timing of events controlled by the RFID reader processor 640 and may couple a date-time stamp to the amount of RFID information 701. A RFID reader power source 630 may include a voltage regulator to provide, for example, a potential of 12 volts and a direct current in the range of 3.5-4.5 amperes.

The RFID reader 602 may include modules which can be stored in the first RFID reader memory 636 of the RFID reader 602 (or could be located in the livestock management server 706 or in the user computing device 614). The RFID reader application 622 stored and implemented by the hardware described herein can include an electromagnetic induction monitor module 662, which functions to monitor current inductance levels in the electromagnetic drive antenna. An electromagnetic inductance calculator module 656 may function to compare current electromagnetic inductance levels to a target electromagnetic inductance level. An electromagnetic inductance controller 664 may function to adjust a current electromagnetic inductance level toward the target electromagnetic inductance level.

A packet receiver module 644 receives the RFID data signal transmitted with the radio-frequency carrier signal from the RFID devices 606. The receiver module 644 can be activated by detection of movement of an RFID device 606 in the electromagnetic field generated by the electromagnetic field generator 624. The receiver module 644 transfers the RFID data signal, which can be decoded by a decoder module 646. The decoder module 646 can be activated by the receiver module 644 and can further function to separate RFID information 701 from a plurality of bit segments 708, 709, 710, 714 received from an RFID device 606. The decoder encoder module 646 can, as to certain RFID information 701, activate a RFID reader calculator module 650 to perform calculation functions and generate RFID object characteristic values 722 from sensed RFID object information 716. A data encoder module 654 may function to assemble transmitted RFID information 701 of the bit segments 708, 709, 710, 712, 714 received from an RFID device. The data encoder 654 may also transfer data packets output from the RFID reader data encoder module 654. A serial packet manager 658 may handle data packets output from the data encoder module 654 to the communication port 634 for LAN or WAN transmission. A communication port enumerator module 652 functions to assign communication port information for a port controller module 660 which functions to control communications between the reader 602 and the livestock management server 706 and/or the user computing device 614.

FIG. 7 is a workflow diagram 700 showing one example of RFID data being transferred from an RFID device (in this example the bolus 606) to the livestock management server 706 via the user computing device 614. In this example, the bolus 606 includes a RFID circuit, for example, located in a hollow inside the bolus 606. The RFID circuit comprises a first bit segment that can be encoded or re-encoded with an amount of RFID object identification segment 709 information (which can be a bolus identification number, animal identifier, and/or the like). A second bit segment of the RFID circuit can be encoded or re-encoded from time to time with sensed RFID object characteristics 710 received from a sensor at the bolus 606, such as a temperature sensor. Other sensed characteristics may include, for example, location, temperature, pH, heart rate, blood pressure, partial pressures of dissolved gases, or the like. Variation of the sensed RFID object characteristic(s) 710 can be continuously or intermittently updated by encoding or re-encoding the second bit segment 710 of the RFID circuit. A third bit segment of the RFID circuit can be encoded or re-encoded from time to time with an amount of calibration data 712 which allows a RFID object characteristic value 722 to be calculated from the sensed RFID object characteristic 710.

The RFID object identification information 709, the sensed RFID object characteristics 710, and the amount of calibration data 712 can be collected from the corresponding bit segments of the RFID circuit by the RFID reader 602 when the RFID object, in this example, the bolus 606, passes within sufficiently close proximity of the RFID reader 602. In certain examples of the RFID reader 602, the RFID object identification 709 information and the sensed RFID object characteristics at sensor data 710 and the calibration data 712 can be received by the RFID reader 602 and coupled to a time-date stamp 728 (which, for example, can take the form of HH:MM:SS and MM/DD/YY). An actual parameter 724 is determined from the sensor data 716 and the calibration data 718. The RFID object characteristic value 722 can be calculated by operation of a RFID reader calculator module 650 having a location in the RFID reader 602 or in the livestock management server 706 or the user computing device 614 (as to certain embodiments) using the sensed RFID object characteristic 650 and the calibration data 712. A parity segment 720 can be located at the beginning and the end of the RFID information 701 from a plurality of bit segments 708, 709, 710, 712, 714 to identify the start and the stop of the RFID information 701.

The RFID object identification information 709 and the sensed RFID object characteristics value 722 can be separated, sorted, and loaded into a current reads database table 730 stored in the user computing device 614. The user computing device 614 may provide the values stored at the current reads database table 730 to the livestock management server 706, where they may be stored at a database table 732 of a datastore of FIG. 1, for later use, as described herein.

Figure 8:
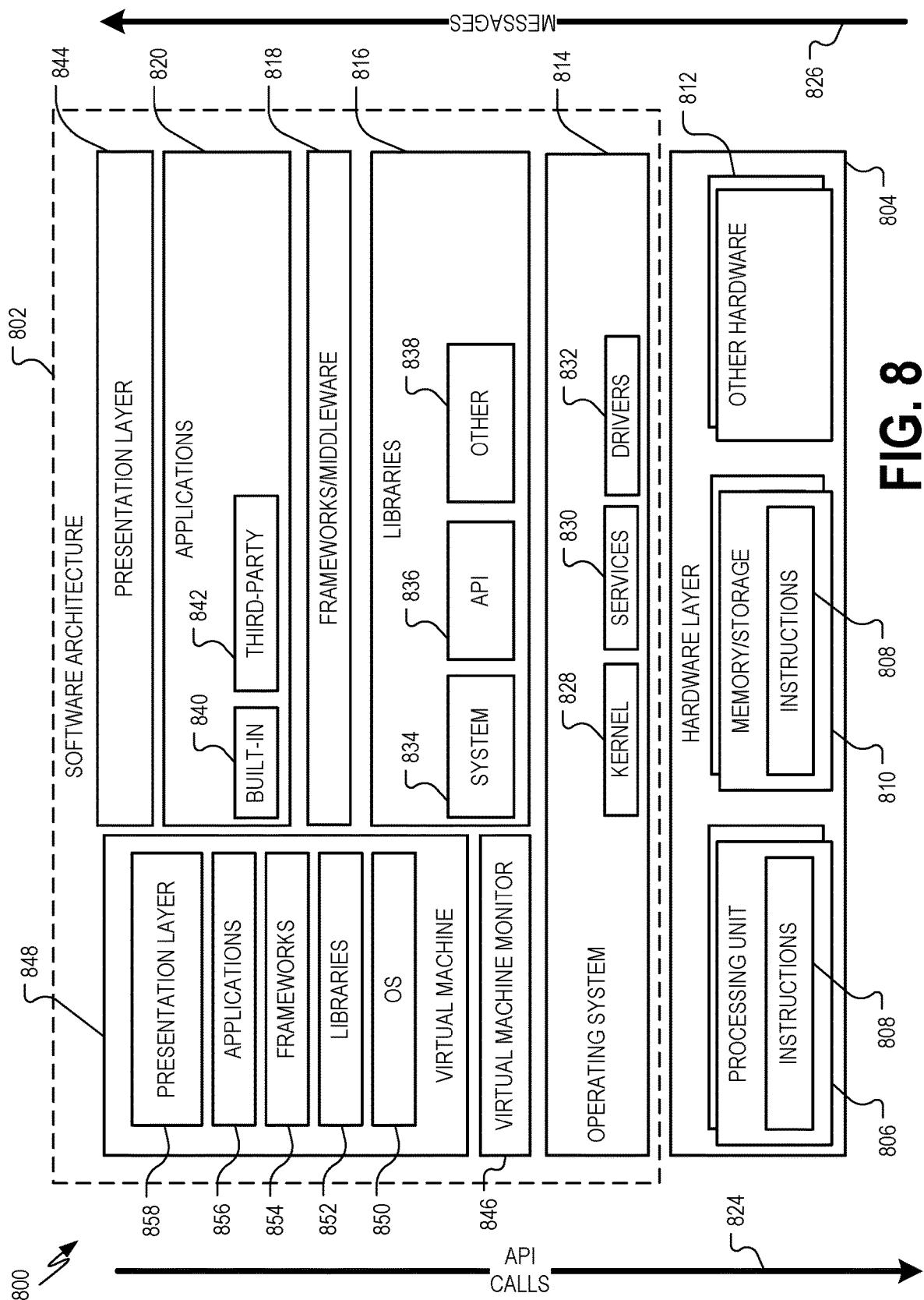
FIG. 8 is a block diagram showing one example of a software architecture for a computing device.

FIG. 8 is a block diagram 800 showing one example of a software architecture 802 for a computing device. The architecture 802 may be used in conjunction with various hardware architectures, for example, as described herein. FIG. 8 is merely a non-limiting example of a software architecture and many other architectures may be implemented to facilitate the functionality described herein. A representative hardware layer 804 is illustrated and can represent, for example, any of the above referenced computing devices. In some examples, the hardware layer 804 may be implemented according to the architecture of the computer system of FIG. 8.

The representative hardware layer 804 comprises one or more processing units 806 having associated executable instructions 808. Executable instructions 808 represent the executable instructions of the software architecture 802, including implementation of the methods, modules, subsystems, and components, and so forth described herein and may also include memory and/or storage modules 810, which also have executable instructions 808. Hardware layer 804 may also comprise other hardware as indicated by other hardware 812 which represents any other hardware of the hardware layer 804, such as the other hardware illustrated as part of the architecture 802.

In the example architecture of FIG. 8, the software architecture 802 may be conceptualized as a stack of layers where each layer provides particular functionality. For example, the software architecture 802 may include layers such as an operating system 814, libraries 816, frameworks/middleware 818, applications 820, and presentation layer 844. Operationally, the applications 820 and/or other components within the layers may invoke Application Programming Interface calls 824 through the software stack and access a response, returned values, and so forth illustrated as messages 826 in response to the API calls 824. The layers illustrated are representative in nature and not all software architectures have all layers. For example, some mobile or special purpose operating systems may not provide a frameworks/middleware layer 818, while others may provide such a layer. Other software architectures may include additional or different layers.

The operating system 814 may manage hardware resources and provide common services. The operating system 814 may include, for example, a kernel 828, services 830, and drivers 832. The kernel 828 may act as an abstraction layer between the hardware and the other software layers. For example, the kernel 828 may be responsible for memory management, processor management (e.g., scheduling), component management, networking, security settings, and so on. The services 830 may provide other common services for the other software layers. In some examples, the services 830 include an interrupt service. The interrupt service may detect the receipt of an interrupt and, in response, cause the architecture 802 to pause its current processing and execute an interrupt service routine (ISR) when an interrupt is accessed.

The drivers 832 may be responsible for controlling or interfacing with the underlying hardware. For instance, the drivers 832 may include display drivers, camera drivers, Bluetooth® drivers, flash memory drivers, serial communication drivers (e.g., Universal Serial Bus (USB) drivers), Wi-Fi® drivers, NFC drivers, audio drivers, power management drivers, and so forth depending on the hardware configuration.

The libraries 816 may provide a common infrastructure that may be utilized by the applications 820 and/or other components and/or layers. The libraries 816 typically provide functionality that allows other software modules to perform tasks in an easier fashion than to interface directly with the underlying operating system 814 functionality (e.g., kernel 828, services 830 and/or drivers 832). The libraries 816 may include system 834 libraries (e.g., C standard library) that may provide functions such as memory allocation functions, string manipulation functions, mathematic functions, and the like. In addition, the libraries 816 may include API libraries 836 such as media libraries (e.g., libraries to support presentation and manipulation of various media format such as MPEG4, H.264, MP3, AAC, AMR, JPG, PNG), graphics libraries (e.g., an OpenGL framework that may be used to render 2D and 3D in a graphic content on a display), database libraries (e.g., SQLite that may provide various relational database functions), web libraries (e.g., WebKit that may provide web browsing functionality), and the like. The libraries 816 may also include a wide variety of other libraries 838 to provide many other APIs to the applications 820 and other software components/modules.

The frameworks 818 (also sometimes referred to as middleware) may provide a higher-level common infrastructure that may be utilized by the applications 820 and/or other software components/modules. For example, the frameworks 818 may provide various graphic user interface (GUI) functions, high-level resource management, high-level location services, and so forth. The frameworks 818 may provide a broad spectrum of other APIs that may be utilized by the applications 820 and/or other software components/modules, some of which may be specific to a particular operating system or platform.

The applications 820 includes built-in applications 840 and/or third-party applications 842. Examples of representative built-in applications 840 may include, but are not limited to, a contacts application, a browser application, a book reader application, a location application, a media application, a messaging application, and/or a game application. Third-party applications 842 may include any of the built in applications as well as a broad assortment of other applications. In a specific example, the third-party application 842 (e.g., an application developed using the Android™ or iOS™ software development kit (SDK) by an entity other than the vendor of the particular platform) may be mobile software running on a mobile operating system such as iOS™ Android™, Windows® Phone, or other mobile computing device operating systems. In this example, the third-party application 842 may invoke the API calls 824 provided by the mobile operating system such as operating system 814 to facilitate functionality described herein.

The applications 820 may utilize built in operating system functions (e.g., kernel 828, services 830 and/or drivers 832), libraries (e.g., system 834, APIs 836, and other libraries 838), and frameworks/middleware 818 to create user interfaces to interact with users of the system. Alternatively, or additionally, in some systems interactions with a user may occur through a presentation layer, such as presentation layer 844. In these systems, the application/module "logic" can be separated from the aspects of the application/module that interact with a user.

Some software architectures utilize virtual machines. In the example of FIG. 8, this is illustrated by virtual machine 848. A virtual machine creates a software environment where applications/modules can execute as if they were executing on a hardware computing device. A virtual machine is hosted by a host operating system (operating system 814) and typically, although not always, has a virtual machine monitor 846, which manages the operation of the virtual machine as well as the interface with the host operating system (i.e., operating system 814). A software architecture executes within the virtual machine such as an operating system 850, libraries 852, frameworks/middleware 854, applications 856 and/or presentation layer 858. These layers of software architecture executing within the virtual machine 848 can be the same as corresponding layers previously described or may be different.

Modules, Components and Logic

Certain embodiments are described herein as including logic or a number of components, modules, or mechanisms. Modules may constitute either software modules (e.g., code embodied (1) on a non-transitory machine-readable medium or (2) in a transmission signal) or hardware-implemented modules. A hardware-implemented module is a tangible unit capable of performing certain operations and may be configured or arranged in a certain manner. In example embodiments, one or more computer systems (e.g., a standalone, client, or server computer system) or one or more hardware processors may be configured by software (e.g., an application or application portion) as a hardware-implemented module that operates to perform certain operations as described herein.

In various embodiments, a hardware-implemented module may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or another programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses that connect the hardware-implemented modules). In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and store the output of that operation in a memory device to which it is communicatively coupled. A further hardware-implemented module may then, at a later time, access the memory device to retrieve and process the stored output. Hardware-implemented modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment, or a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., APIs).

Electronic Apparatus and System

Example embodiments may be implemented in digital electronic circuitry, or in computer hardware, firmware, or software, or in combinations of them. Example embodiments may be implemented using a computer program product, e.g., a computer program tangibly embodied in an information carrier, e.g., in a machine-readable medium for execution by, or to control the operation of, data processing apparatus, e.g., a programmable processor, a computer, or multiple computers.

A computer program can be written in any form of programming language, including compiled or interpreted languages, and it can be deployed in any form, including as a standalone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., an FPGA or an ASIC.

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures merit consideration. Specifically, it will be appreciated that the choice of whether to implement certain functionality in permanently configured hardware (e.g., an ASIC), in temporarily configured hardware (e.g., a combination of software and a programmable processor), or in a combination of permanently and temporarily configured hardware may be a design choice. Below are set out hardware (e.g., machine) and software architectures that may be deployed, in various example embodiments.

Example Machine Architecture and Machine-Readable Medium

Figure 9:
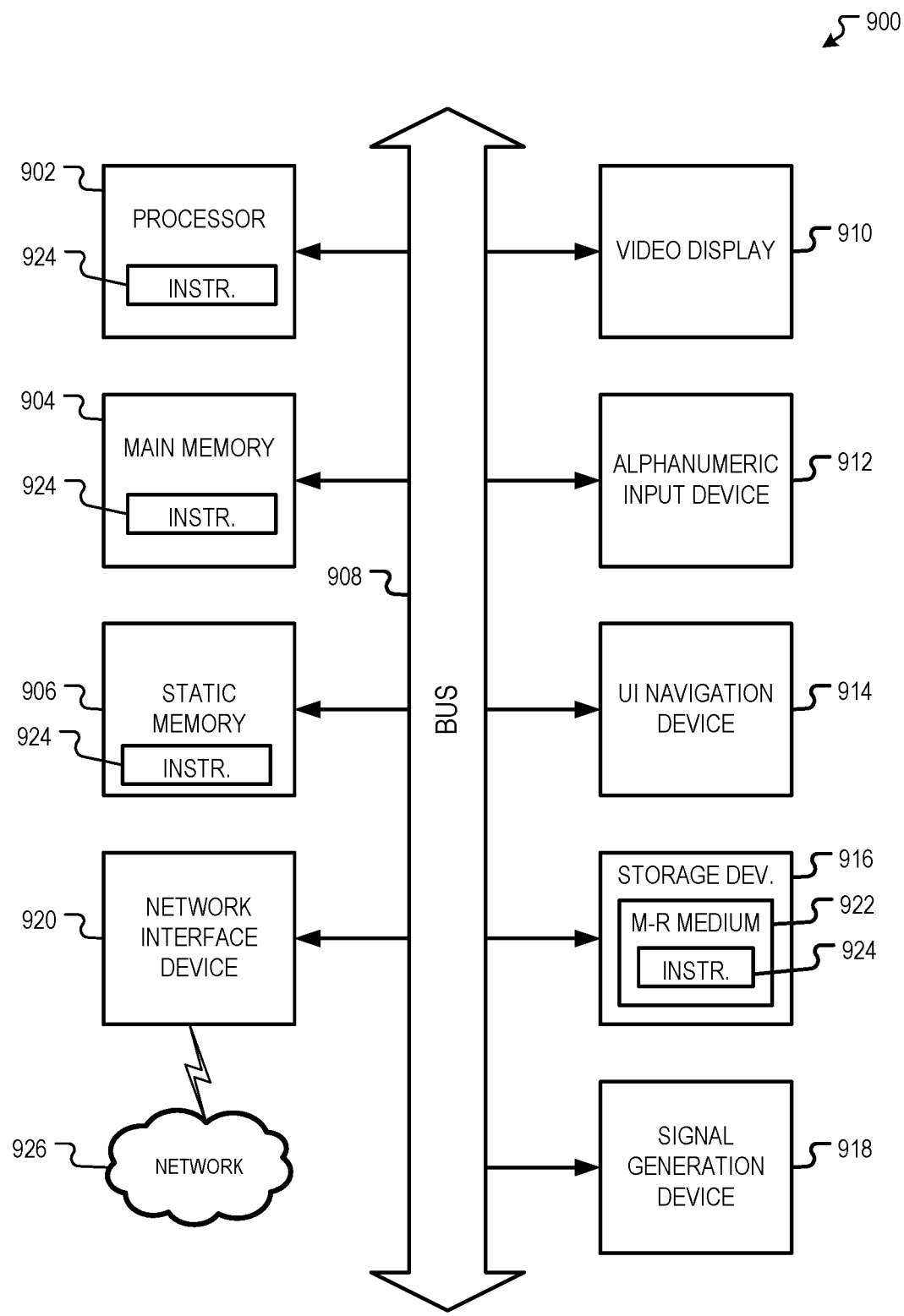
FIG. 9 is a block diagram of a machine in the example form of a computer system within which instructions may be executed for causing the machine to perform any one or more of the methodologies discussed herein.

FIG. 9 is a block diagram of a machine in the example form of a computer system 900 within which instructions 924 may be executed for causing the machine to perform any one or more of the methodologies discussed herein. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch, or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 900 includes a processor 902 (e.g., a central processing unit (CPU), a graphics processing unit (GPU), or both), a main memory 904, and a static memory 906, which communicate with each other via a bus 908. The computer system 900 may further include a video display unit 910 (e.g., a liquid crystal display (LCD) or a cathode ray tube (CRT)). The computer system 900 also includes an alphanumeric input device 912 (e.g., a keyboard or a touch-sensitive display screen), a user interface (UI) navigation (or cursor control) device 914 (e.g., a mouse), a disk drive unit 916, a signal generation device 918 (e.g., a speaker), and a network interface device 920.

Machine-Readable Medium

The disk drive unit 916 includes a machine-readable medium 922 on which is stored one or more sets of data structures and instructions 924 (e.g., software) embodying or utilized by any one or more of the methodologies or functions described herein. The instructions 924 may also reside, completely or at least partially, within the main memory 904 and/or within the processor 902 during execution thereof by the computer system 900, with the main memory 904 and the processor 902 also constituting machine-readable media 922.

While the machine-readable medium 922 is shown in an example embodiment to be a single medium, the term "machine-readable medium" may include a single medium or multiple media (e.g., a centralized or distributed database, and/or associated caches and servers) that store the one or more instructions 924 or data structures. The term "machine-readable medium" shall also be taken to include any tangible medium that is capable of storing, encoding, or carrying instructions 924 for execution by the machine and that cause the machine to perform any one or more of the methodologies of the present disclosure, or that is capable of storing, encoding, or carrying data structures utilized by or associated with such instructions 924. The term "machine-readable medium" shall accordingly be taken to include, but not be limited to, solid-state memories, and optical and magnetic media. Specific examples of machine-readable media 922 include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; and CD-ROM and DVD-ROM disks.

Transmission Medium

The instructions 924 may further be transmitted or received over a communications network 926 using a transmission medium. The instructions 924 may be transmitted using the network interface device 920 and any one of a number of well-known transfer protocols (e.g., HTTP). Examples of communication networks include a (LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding, or carrying instructions 924 for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the disclosure. Accordingly, the specification and drawings are to be regarded in an illustrative rather than a restrictive sense. The accompanying drawings that form a part hereof show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A livestock monitoring method comprising:
   accessing a motion sensor signal generated by an animal bolus sensor located within the reticulum or rumen of a non-human mammal, the motion sensor signal comprising a rotational component describing a rotational motion of the sensor within an animal and a linear component describing a linear movement of the sensor within the animal;
   identifying an animal respiration signal with the rotational component of the motion sensor signal;
   generating a respiration-corrected linear component through use of the linear component of the motion sensor signal and the animal respiration signal; and
   detecting an animal heart signal from the respiration-corrected linear component.

2. The method of claim 1, wherein the rotational component of the motion sensor signal comprises a rotational magnitude component describing a magnitude of the rotation of the sensor within the animal; and wherein the linear component of the motion sensor signal comprises a linear magnitude component describing a magnitude of the linear movement of the sensor within the animal; the method further comprising:
   detecting at least one acceleration peak of the rotational magnitude component; and
   correlating the at least one acceleration peak of the rotational magnitude component to at least one correlated acceleration peak of the linear magnitude component, the generating of the respiration-corrected linear component comprising removing the at least one correlated acceleration peak of the linear magnitude component of the motion sensor signal to generate a respiration-corrected linear magnitude.

3. The method of claim 2, further comprising, before detecting the at least one acceleration peak of the rotational magnitude component, applying a first bandpass filter to the rotational magnitude component of the motion sensor signal, the first bandpass filter having a passband corresponding to an expected respiration rate of the animal.

4. The method of claim 2, wherein the generating of the respiration-corrected linear component further comprises applying a second bandpass filter to the respiration-corrected linear magnitude component to generate a filtered respiration-corrected linear magnitude component, the second bandpass filter having a passband corresponding to a first expected heart rate range for the animal.

5. The method of claim 4, further comprising:
   determining that the filtered respiration-corrected linear magnitude component does not indicate the animal heart rate; and
   applying a third bandpass filter to the respiration-corrected linear magnitude component to generate a second filtered linear magnitude component, the third bandpass filter having a passband different than the passband of the second bandpass filter, wherein the detecting of the animal heart signal uses the second filtered linear magnitude component.

6. The method of claim 1, further comprising:
   determine a down direction through use of the rotational component;
   identifying at least one acceleration peak of the rotational component directed towards the down direction; and
   correlating the at least one acceleration peak of rotational component directed towards the down direction to at least one correlated acceleration peak of the linear component, wherein the generating of the respiration-corrected linear component comprises removing the at least one correlated acceleration peak from the linear component.

7. The method of claim 1, further comprising:
sending, by a collection device, an interrogation signal to an animal bolus comprising the animal bolus sensor; and
receiving the animal motion sensor signal by the collection device and from the animal bolus.

8. The method of claim 1, further comprising:
determining that an animal heart rate indicated by the animal heart signal is outside of an animal heart rate range; and
sending a heart rate alert to a user computing device.

9. A livestock monitoring system comprising:
at least one hardware processor programmed to perform operations comprising:
accessing an animal motion sensor signal generated by an animal bolus sensor located within the reticulum or rumen of a non-human mammal, wherein the animal motion sensor signal comprises a rotational component describing a rotational motion of the sensor within an animal and a linear component describing a linear movement of the sensor within the animal;
identifying an animal respiration signal with the rotational component of the motion sensor signal;
generating a respiration-corrected linear component through use of the linear component of the motion sensor signal and the animal respiration signal; and
detecting an animal heart signal from the respiration-corrected linear component.

10. The system of claim 9, wherein the rotational component of the motion sensor signal comprises a rotational magnitude component describing a magnitude of the rotation of the sensor within the animal; wherein the linear component of the motion sensor signal comprises a linear magnitude component describing a magnitude of the linear movement of the sensor within the animal; the operations further comprising:
detecting at least one acceleration peak of the rotational magnitude component; and
correlating the at least one acceleration peak of the rotational magnitude component to at least one correlated acceleration peak of the linear magnitude component, wherein the generating of the respiration-corrected linear component comprises removing the at least one correlated acceleration peak of the linear magnitude component of the motion sensor signal to generate a respiration-corrected linear magnitude.

11. The system of claim 10, the operations further comprising, before detecting the at least one acceleration peak of the rotational magnitude component, applying a first bandpass filter to the rotational magnitude component of the motion sensor signal, the first bandpass filter having a passband corresponding to an expected respiration rate of the animal.

12. The system of claim 10, the generating of the respiration-corrected linear component further comprising applying a second bandpass filter to the respiration-corrected linear magnitude component to generate a filtered respiration-corrected linear magnitude component, the second bandpass filter having a passband corresponding to a first expected heart rate range for the animal.

13. The system of claim 12, the operations further comprising:
determining that the filtered respiration-corrected linear magnitude component does not indicate the animal heart rate; and
applying a third bandpass filter to the respiration-corrected linear magnitude component to generate a second filtered linear magnitude component, the third bandpass filter having a passband different than the passband of the second bandpass filter, the detecting of the animal heart signal through use of the second filtered linear magnitude component.

14. The system of claim 9, the operations further comprising:
determining a down direction through use of the rotational component;
identifying at least one acceleration peak of the rotational component directed towards the down direction; and
correlating the at least one acceleration peak of rotational component directed towards the down direction to at least one correlated acceleration peak of the linear component, wherein the generating of the respiration-corrected linear component comprises removing the at least one correlated acceleration peak from the linear component.

15. The system of claim 9, the operations further comprising:
sending, by a collection device, an interrogation signal to an animal bolus comprising the animal bolus sensor; and
receiving the animal motion sensor signal by the collection device and from the animal bolus.

16. The system of claim 9, the operations further comprising:
determining that an animal heart rate indicated by the animal heart signal is outside of an animal heart rate range; and
sending a heart rate alert to a user computing device.

17. A non-transitory machine-readable medium comprising instructions thereon that, when executed by at least one hardware processor, causes the at least one hardware processor to perform operations comprising:
accessing an animal motion sensor signal generated by an animal bolus sensor located within the reticulum or rumen of a non-human mammal, wherein the animal motion sensor signal comprises a rotational component describing a rotation of the sensor within an animal and a linear component describing a linear movement of the sensor within the animal;
identifying an animal respiration signal with the rotational component of the motion sensor signal;
generating a respiration-corrected linear component through use of the linear component of the motion sensor signal and the animal respiration signal; and
detecting an animal heart signal from the respiration-corrected linear component.

18. The medium of claim 17, wherein the rotational component of the motion sensor signal comprises a rotational magnitude component describing a magnitude of the rotation of the sensor within the animal; wherein the linear component of the motion sensor signal comprises a linear magnitude component describing a magnitude of the linear movement of the sensor within the animal; the operations further comprising:
detecting at least one acceleration peak of the rotational magnitude component; and
correlating the at least one acceleration peak of the rotational magnitude component to at least one correlated peak of the linear magnitude component, the generating of the respiration-corrected linear component comprising removing the at least one correlated peak of the linear magnitude component of the motion sensor signal to generate a respiration-corrected linear magnitude.

19. The medium of claim 18, wherein the generating of the respiration-corrected linear component further comprises applying a second bandpass filter to the respiration-corrected linear magnitude component to generate a filtered respiration-corrected linear magnitude component, the second bandpass filter having a passband corresponding to a first expected heart rate range for the animal.

20. The medium of claim 17, the operations further comprising:
 determining a down direction through use of the rotational component;
 identifying at least one peak of the rotational component directed towards the down direction; and
 correlating the at least one peak of rotational component directed towards the down direction to at least one correlated peak of the linear component, the generating of the respiration-corrected linear component comprising removing the at least one correlated peak from the linear component.

* * * * *